United States Patent [19]

Arndt et al.

[11] Patent Number: 4,517,380

[45] Date of Patent: May 14, 1985

[54] METHOD FOR PURIFYING METHACRYLAMIDOPROPYL TRIMETHYLAMMONIUM CHLORIDE AND RELATED COMPOUNDS

[75] Inventors: Peter J. Arndt, Seeheim-Jugenheim; Manfred Müller, Rossdorf; Fritz Schlosser; Franz Wenzel, both of Darmstadt, all of Fed. Rep. of Germany

[73] Assignee: Röhm GmbH, Darmstadt, Fed. Rep. of Germany

[21] Appl. No.: 626,443

[22] Filed: Jun. 29, 1984

[30] Foreign Application Priority Data

Aug. 5, 1983 [DE] Fed. Rep. of Germany ....... 3328350

[51] Int. Cl.³ ............................................ C07C 103/44
[52] U.S. Cl. ..................................... 564/206; 560/218
[58] Field of Search ........................ 564/206; 560/218

[56] References Cited

U.S. PATENT DOCUMENTS

| | | | |
|---|---|---|---|
| 3,878,247 | 4/1975 | Moss et al. | 260/561 N |
| 3,907,891 | 9/1975 | Guilbault et al. | 564/206 |
| 4,206,143 | 6/1980 | Wenzel et al. | 260/561 N |
| 4,375,558 | 3/1983 | McEntire et al. | 564/206 |

FOREIGN PATENT DOCUMENTS 3048020 7/1982 German Democratic Rep. .................................. 564/206

Primary Examiner—Paul F. Shaver
Attorney, Agent, or Firm—Curtis, Morris & Safford

[57] ABSTRACT

Methacrylamidopropyl trimethylammonium chloride and similar quaternized aminoalkyl esters or aminoalkylamides of acrylic acid or methacrylic acid are purified by extraction of an aqueous solution thereof with dichloromethane to remove impurities, such as allyl methacrylamide, which may be formed by a Hofmann degradation of the compounds.

2 Claims, No Drawings

METHOD FOR PURIFYING METHACRYLAMIDOPROPYL TRIMETHYLAMMONIUM CHLORIDE AND RELATED COMPOUNDS

The present invention relates to a method for the purification of methacrylamidopropyl trimethylammonium chloride (MAPTAC) or related compounds by the removal of polyunsaturated impurities which have a crosslinking effect in polymerization.

MAPTAC can be obtained by quaternization of N-dimethylaminopropyl methacrylamide with methyl chloride. Various methods are known for preparing the starting compound. According to German Pat. No. 2,502,247, N-dimethylaminopropyl methacrylamide is obtained by reacting methyl methacrylate with twice the molar amount of dimethylaminopropylamine and thermally decomposing the Michael adduct so formed. A simpler route to formation of this compound is the aminolysis of methyl methacrylate with dimethylaminopropylamine in the presence of dialkyltin oxide as a catalyst in accordance with German Pat. No. 2,816,516, and preferably also in the presence of an alkyl titanate according to published German patent application Ser. No. DOS 30 48 020.

The quaternization products of MAPTAC can be polymerized in aqueous solution to give high molecular weight polycationic polymers or copolymers which are highly effective sedimentation aids and flocculants. In such polymerizations, disturbances have been observed which in all likelihood are due to small traces of impurities that have a crosslinking effect. These disturbances manifest themselves in that a 1% aqueous solution of the polymer obtained contains gelatinous insoluble residues, or in that the polymer itself is insoluble in water. It has been found that these disturbances are the more pronounced the more N-allyl methacrylamide is contained in the MAPTAC as an impurity. Preparations containing less than 10 ppm of N-allyl methacrylamide have been found to be substantially free of such disturbances. However, up to now such preparations have had to be produced by complicated processes which do not lend themselves to industrial use.

The formation of N-allyl methacrylamide from MAPTAC may be attributable to Hofmann degradation in accordance with the reaction equation.

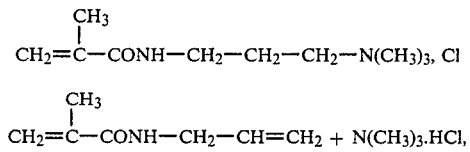

although it has not been established that it is formed in this way. N-allyl methacrylamide is often detected in concentrations of over 10 ppm, for example of 40 to 100 ppm or even higher. However, it is by no means certain that N-allyl methacrylamide is the only or principal cause of the disturbances. Rather, it would appear that MAPTAC usually contains a number of impurities which are always accompanied by N-allyl methacrylamide.

The object of the invention is to provide a method for the preparation of MAPTAC and related compounds which are free of troublesome impurities, and which in particular contain less than 10 ppm of N-allyl methacrylamide, by a route which readily lends itself to industrial use. It has been found that this can be done by extraction of an aqueous solution of MAPTAC with dichloromethane.

The invention is not limited to MAPTAC but can be similarly used with compounds of the formula

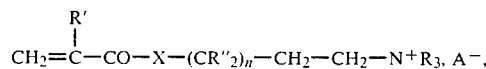

wherein R represents the same or different alkyl groups, $A^-$ is an anion of an acid, $R'$ is hydrogen or methyl, $R''$ is hydrogen or lower alkyl, X is oxygen or —NH—, and n is an integer from 0 to 3. The characteristic which these compounds have in common is the ability to be converted, through Hofmann degradation, into a diunsaturated compound of the formula

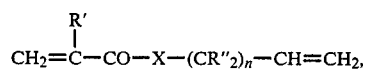

and an ammonium salt, $NR_3 \cdot HA$. The polymerizability of the —CH=CH$_2$ group may be the principal cause of the observed disturbances since it can trigger the crosslinking of the polymer of the undegraded compound.

Among the compounds to which the invention is applicable, derivatives of methacrylic acid wherein $R'$ is methyl are preferred. Compounds with an amide structure which contain an —NH— group as X are also preferred. The $CR''_2$ group usually is methylene, although other alkylidene groups such as ethylidene, isopropylidene, or isobutylidene groups are also suitable for use. $R''$ preferably comprises no more than two carbon atoms. When n is greater than 1, the groups ($CR''_2$) may also be different. The moieties R on the nitrogen atom may be the same or different and preferably have from 1 to 4 carbon atoms, methyl groups being preferred. $A^-$ is preferably derived from a mineral acid, from partial esters of a mineral acid, or from an organic sulfonic acid. The preferred acid ions $A^-$ are methosulfate and particularly chloride. However, other anions such as sulfate (or a half equivalent thereof), hydrogen sulfate (bisulfate), bromide, iodide, benzene sulfonate, or toluene sulfonate are also suitable for use.

Highly preferred compounds for treatment according to the invention are methacrylamidopropyl trimethylammonium-chloride and -methosulfate. Other preferred compounds are the corresponding acrylamide compounds as well as acryl- or methacryl-oxyethyl trimethylammonium chloride or the corresponding methosulfate.

The invention is based on the fact that the polyunsaturated degradation products and possible further accompanying impurities are readily soluble in dichloromethane whereas the salt-like non-degraded starting compounds are completely insoluble therein. Other organic solvents, such as perchloroethylene, have proved unsuitable for the extraction of these impurities.

The concentration of the aqueous solution of the compound being treated is of no consequence to the process of the invention, provided that extremely dilute solutions are not used. The solutions used are preferably at least 20% solutions, and are particularly solutions at or near saturation concentration at the extraction temperature. For MAPTAC, concentrations ranging from 40 to 90 weight percent have been found suitable.

For the extraction, substantially pure dichloromethane is preferred. However, solvent mixtures comprising at least 50 weight percent of dichloromethane together with one or more other water immicible solvents, such as other chlorinated hydrocarbons, or aromatic or aliphatic hydrocarbons, generally are suitable for use.

The amount of dichloromethane may be between 0.2 and 10 times the weight of the aqueous solution, for example. In batchwise operation, the purifying effect will be enhanced if the extractant is divided into several portions and the aqueous solution is extracted repeatedly with the individual portions.

As usual, the extraction involves at least short-time intimate mixing of the phases which are not soluble in each other, followed by phase separation. Which of the phases is divided into droplets in the other is immaterial. In batchwise operation, agitated vessels with an efficient agitator and a bottom valve are suitable for use. In continuous operation, a conventional liquid-phase extraction column with static or dynamic mixing devices, optionally followed by a settling chamber, may be used. After distillation, the extractant may be reused in the process of the invention.

The extraction is usually carried out at room temperature, and more particularly in the range from 15° to 30° C. However, higher or lower temperatures may readily be employed. A higher extraction temperature may be advisable when it is desired to operate with a higher saturation concentration of the aqueous solution, but temperatures above the boiling point of the extractant are not recommended because of the pressure equipment which would then be required.

As a rule, the content of polyunsaturated compounds in the aqueous solution after one extraction stage, or after three extraction stages at most, will be less than 10 ppm. The solution so purified can be used directly to produce uncrosslinked, extremely high molecular weight homo- or co-polymers of the undegraded compound in the form of an aqueous polymer solution or of a soluble gel. If desired, the solution may be evaporated to dryness to obtain the purified compound in pure form. This should be done under mild conditions to prevent a recurrence of impurity formation by Hofmann degradation.

A better understanding of the present invention and of its many advantages will be had by referring to the following specific Example, given by way of illustration.

EXAMPLE 1

1,000 g of a 50% aqueous solution of MAPTAC containing 45 ppm of N-allyl methacrylamide (as determined by high-pressure liquid chromatography) is intensively mixed with (a) two 500 ml portions of dichloromethane or (b) three 200 ml portions of dichloromethane in a separatory funnel and separated each time after the dichloromethane has settled. Only traces of less than 0.1 ppm of N-allyl methacrylates are detectable in the third portion of extractant.

In both cases, less than 1 ppm of N-allyl methacrylamide is then detectable in the purified solution. Polymers prepared from this purified monomer give homogenous solutions of a viscosity ranging from 6,000 to 10,000 mPa.sec. when dissolved in water in a concentration of 1%.

COMPARISON EXAMPLE

After being extracted with four 500 ml portions of perchloroethylene, the N-allyl methacrylamide content of the MAPTAC solution used is found to be practically unchanged.

What is claimed is:

1. A method for purifying a compound of the formula

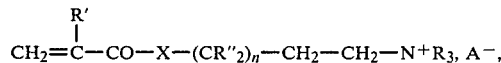

by the removal of impurities therefrom, including an impurity of the formula

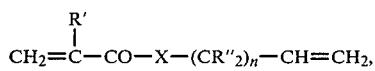

wherein R is the same or different alkyl, R' is hydrogen or methyl, R" is hydrogen or lower alkyl, X is oxygen or —NH—, A$^-$ is an anion of an acid, and n is an integer from 0 to 3, which method comprises extracting an aqueous solution of said compound with dichloromethane.

2. A method as in claim 1 wherein said compound is methacrylamidopropyl trimethylammonium chloride containing N-allyl methacrylamide as an impurity.

* * * * *